(12) United States Patent
Chang et al.

(10) Patent No.: US 6,645,719 B2
(45) Date of Patent: Nov. 11, 2003

(54) HERBAL CHIP

(75) Inventors: Su-Chen Chang, Taichung (TW); Li-Wei Hsu, Taichung (TW); Jyh-Phen Chen, Taipei (TW); Jeng-Woei Lee, Yung He (TW)

(73) Assignee: Advanced Gene Technology Corporation (TW)

( * ) Notice: Subject to any disclaimer, the term of this patent is extended or adjusted under 35 U.S.C. 154(b) by 0 days.

(21) Appl. No.: 09/875,361

(22) Filed: Jun. 5, 2001

(65) Prior Publication Data

US 2002/0182715 A1 Dec. 5, 2002

(51) Int. Cl.⁷ .................................................. C12Q 1/68
(52) U.S. Cl. ......................................................... 435/6
(58) Field of Search ........................... 564/84; 514/444; 536/25.3, 22.1, 23.1, 25.4; 435/6

(56) References Cited

U.S. PATENT DOCUMENTS

| | | | | | |
|---|---|---|---|---|---|
| 5,714,608 | A | * | 2/1998 | Gerster | 546/82 |
| 5,753,692 | A | * | 5/1998 | Chang et al. | 514/444 |
| 6,172,261 | B1 | * | 1/2001 | Vermeulin et al. | 564/84 |
| 6,194,563 | B1 | * | 2/2001 | Cruickshank | 536/25.3 |

FOREIGN PATENT DOCUMENTS

| | | | | |
|---|---|---|---|---|
| CN | 1314493 | | 3/2000 | 435/6 |

* cited by examiner

*Primary Examiner*—Gary Benzion
*Assistant Examiner*—Arun K. Chakrabarti
(74) *Attorney, Agent, or Firm*—Morrison & Foerster LLP

(57) ABSTRACT

The present invention relates to a herbal chip comprising a plastic slide, a coating as a spacer on the plastic slide, and fractions or components obtained from herbs that are independently allocated in microarrays on the coating. The herbal chip is useful for screening for active ingredients contained in the herbs that have specific pharmacological or therapeutical functions.

20 Claims, 3 Drawing Sheets

|   | 1 | 2 | 3 | 4 | 5 | 6 | 7 | 8 | 9 | 10 |
|---|---|---|---|---|---|---|---|---|---|---|
| A | Crude Extract Herb I | | Cy5 reidure | | Cy3 residure | | Fraction 1 Herb A | | Fraction 2 Herb B | |
| B | Fraction 1 Herb C | | Fraction 2 Herb C | | Fraction 3 Herb C | | Fraction 4 Herb C | | Fraction 5 Herb C | |
| C | Fraction 6 Herb C | | Fraction 7 Herb C | | Fraction 8 Herb C | | Fraction 9 Herb C | | heparin | |
| D | Crude Extract Herb D | | Crude Extract Herb E | | Crude Extract Herb F | | Crude Extract Herb G | | Crude Extract Herb H | |
| E | adenosine | | Pure ingredient Herb J | | B-gelatin | | gelatin | | biotin | |
| F | Fibrinogen | | ReoPro | | TNF-αR | | ovalbumin | | BSA | |

Fig 2A

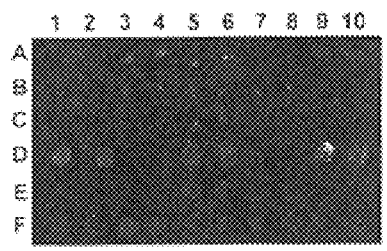

Fig 2B

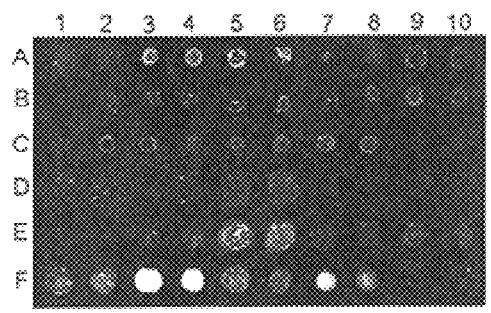

Fig 2C

HERBAL CHIP

TECHNICAL FIELD OF THE INVENTION

The present invention relates to the allocation of fractions or components obtained from herbs in microarrays on a plastic substrate. The plastic substrate containing allocated fractions or components of herbs is useful as a platform for screening for active ingredients contained in the herbs that have specific pharmacological or therapeutical functions.

BACKGROUND OF THE INVENTION

The use of herbs or an extract or fraction thereof as a medicine has been well known for so many years. For example, the bark of willow tree has been used as an antipyretic and analgesic agent for more than 2000 years, and an extract from the bark of Peruvian Cinchona has been used for the treatment of malaria since the $17^{th}$ century.

Up to date, however, only a few active ingredients contained in herbs that have specific pharmacological or therapeutical functions were discovered. For example, salicin, a salicyl alcohol glucoside, was recognized as an active ingredient in the bark of willow tree that exhibited antipyretic and analgesic properties in the middle of $20^{th}$ century, and quinine was recognized as an active ingredient in the bark of Peruvian Cinchona that exhibited an effect on the treatment of malaria in 1820.

The discovery of an active ingredient from a herb was laborious and time-consuming. For example, taxol, an antitumor drug, was isolated from the bark of North American yew tree *Taxus brevifolia*, after the work of screening of more than 110,000 samples derived from more than 35,000 plant genera collected worldwide. In general, he common strategy in the discovery of an active ingredient from a herb was to identify the function(s) of the herb in human body and to apply various physical and chemical procedures for isolating active fraction(s) of the herb and then for separating and purifying the active ingredient. There was no general guideline for the discovery of an active ingredient from a herb. Though the understanding of pathogeny in the molecular or gene level based on the development of pharmacology, cell biology and molecular biology was significantly increasing, and the shotgun screening of an extract of a herb for hitting desired active ingredient(s) contained in the herb was developed, however the discovery of an active ingredient from a herb was still a laborious, trial-and-error work and progressed in a slow pace.

There has been a demand in the art to develop a new tool to conduct a rapid screening for active ingredients from herbs or an extract or fraction thereof that have specific pharmacological or therapeutical functions.

The technique of immobilization of large biological molecules on a solid substrate (e.g. nylon membrane), such as Western blot for immobilizing peptides or proteins, Southern blot for immobilizing DNA fragments and Northern blot for immobilizing RNA fragments, was used in the art, and the immobilized molecules interacted with a labeled probe and then the resultant probe-labeled molecules were imaged. For example, enzyme-linked immunosorbent assay (ELISA) involved immobilizing large biological molecules on a substrate, interacting the immobilized molecules with a labeled substance, and then coloring and imaging the resultant labeled molecule(s). The ELISA could be performed on a conventional 96-well microplate.

Recently, the high-density gridding technology was used in the art for detecting the presence of a target material in biological samples (e.g. DNA or proteins), wherein the samples were immobilized in a predetermined array on a solid substrate (e.g. glass slide) and then were hybridized with a labeled probe, followed by washing and imaging. In applying the high-density gridding technology, the biological samples were known DNA or protein pools that were homogeneous, and the labeled probe was an unknown or unidentified substance that was heterogeneous. The advantage of the high-density gridding technology resided in that a tiny volume of a sample could be immobilized in a small gridded area on the surface of the substrate and thousands of samples could be manipulated simultaneously. Further, a computer-controlled three-axis robot and a unique pen tip assembly (i.e. microarrayer) could be used to generate the high-density, gridded arrays of biological samples on the surface of a substrate.

So far, however, the high-density gridding technology was used for analyzing just macromolecules, such as proteins and nucleic acids, where the immobilize samples on the surface of a solid substrate (e.g. glass slide) were homogeneous. There was no teaching or suggestion in the art that heterogeneous samples containing large, biologically active molecules (such as proteins or nucleic acids) or small, biologically active molecules (such as secondary metabolites) could be immobilized on the surface of a solid substrate (e.g. plastic slide). There was also no teaching or suggestion in the art that homogeneous or heterogeneous samples obtained from herbs or extracts or fractions thereof could be immobilized on the surface of a solid substrate (e.g. plastic slide), especially in a microarray format. Furthermore, there was no teaching or suggestion in the art that by applying the high-density gridding technology, a high throughput screening for biologically active molecules from herbs could be conducted with the homogeneous or heterogeneous, unknown samples allocated on the surface of a solid substrate (e.g. plastic slide) that interacted with homogeneous or heterogeneous, known labeled probe(s).

Therefore, the present invention discloses a new platform for screening for active ingredients from herbs with homogeneous or heterogeneous, known labeled probe(s), which comprises homogeneous or heterogeneous ingredients from herbs that are immobilized on a solid substrate (e.g. plastic slide).

SUMMARY OF THE INVENTION

The present invention discloses a new platform, named herbal chip, comprising a plastic slide, a coating as a spacer on the plastic slide, and fractions or components obtained from herbs that are independently allocated in microarrays on the coating. The herbal chip of the present invention is useful for screening for active ingredients contained in the herbs that have specific pharmacological or therapeutical functions.

The present invention also discloses a method for producing the herbal chip.

Further, the present invention discloses a method of using the herbal chip for screening for active ingredients contained in herbs.

BRIEF DESCRIPTION OF THE FIGURES

FIG. 2A shows an example of the herbal chip of the present invention where samples were gridded with 6×10 matrix on the plastic slide of FIG. 1.

FIG. 2B shows endogenous fluorescence of the gridded samples on the herbal chip shown in FIG. 2A prior to hybridization with labeled probes.

FIG. 2C shows fluorescence image of the gridded samples on the herbal chip shown in FIG. 2A after hybridization with Cy3-labeled TNF-α/R (tumor necrosis factor-alpha receptor) and Cy5-labeled strepavidin.

DETAILED DESCRIPTION OF THE INVENTION

The present invention discloses a new platform, named herbal chip, for shotgun screening for active ingredients contained in herbs in a target-directed manner for achieving high throughput. The herbal chip of the present invention comprises a plastic slide, a coating as a spacer on the plastic slide, and fractions or components obtained from herbs that are independently allocated or immobilized in microarrays on the coating.

In the herbal chip of the present invention, each of the fractions or components obtained from herbs that is spotted in microarrays is substantially an uncharacterized, homogeneous or heterogeneous, partially-purified mixture obtained from the herbs. The fractions or components may be obtained by fractionating an extract of the herb by applying an apparatus, e.g. HPLC. Each of the spots on the herbal chip may comprise secondary metabolites of the herb.

In the herbal chip of the present invention, a plastic slide is used in place of the conventional glass slide. The material of the plastic slide is a homopolymer or copolymer, which is made of one or more monomers selected from the group consisting of ethylene, haloethylene, propylene, halopropylene, acrylate, methacrylate, butadiene, acrylonitrile, norbornene and styrene, wherein a polymer of styrene is preferred. Also included in the material of the plastic slide is polycarbonate. The plastic slide is comparable in size to the ones conventionally used within a microarrayer and a laser scanner. The advantage of using a plastic slide in the herbal chip of the present invention is that there are a variety of chemicals that can be used for treating the surface of a plastic slide, whereby not only macromolecules (such as proteins and DNA) but also micromolecules (such as metabolites of herbs) can be immobilized on the surface of the plastic slide, in view of the fact that conventional glass slide was used for immobilizing just macromolecules, such as protein and DNA.

Figure 1:
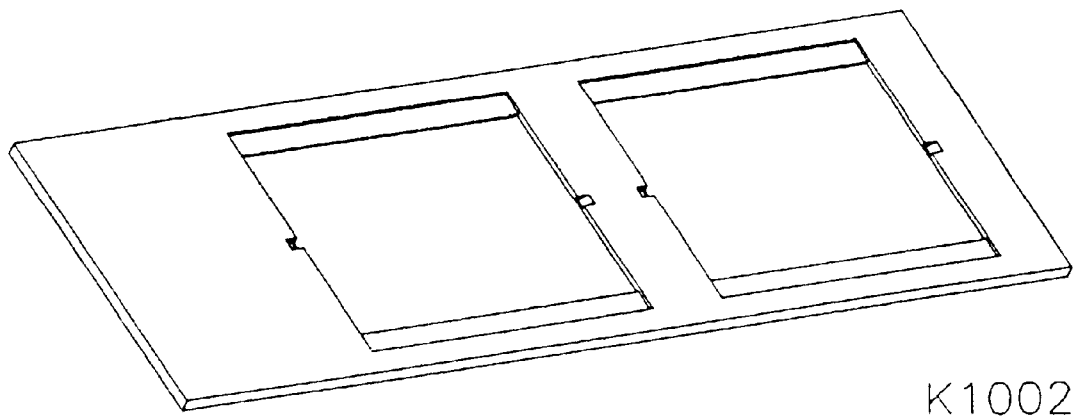
FIG. 1 shows the perspective of a plastic slide for producing the herbal chip of the present invention.

Further, a plastic slide can be easily molded into a shape as desired and is also effective in cost. In an embodiment of the present invention, the plastic slide is molded with two cavity chambers as shown in FIG. 1, based on which samples obtained from fractions or components of a herb can be gridded on the surface of the chambers, and a probe(s)-containing solution for conducting hybridization is then loaded onto the chambers. The depth of the two cavity chambers may be the same or different, and ranges from less than 0.03 mm to up to 0.5 mm. Further, as shown in FIG. 1, two bars are respectively molded at the opposite sides of each chamber for supporting a glass lid, wherein the glass lid is useful for preventing the evaporation or loss of the probe(s)-containing solution loaded onto the chamber.

In the herbal chip of the present invention, the plastic slide is pretreated with a polyfunctional aldehyde followed by soaking in a solution of $NH_2$ group(s)-providing precursor, whereby the resultant plastic slide contains active amino groups on its surface. The $NH_2$ group(s)-providing precursor may be organic or inorganic and may be selected from the group consisting of $NH_4OH$, primary amine, secondary amine and tertiary amine, wherein the aliphatic or aromatic part of the primary amine, secondary amine and tertiary amine may be useful as an additional spacer arm. Among the $NH_2$ group(s)-providing precursors, $NH_4OH$ directly providing free $NH_2$ group is preferred.

In the herbal chip of the present invention, the coating on the plastic slide is made of polyfunctional molecules, e.g. polyfunctional epoxides, as a spacer. The polyfunctional epoxides act for linking the components contained in herbs to the pretreated plastic slide. The active epoxy groups on one end of the polyfunctional epoxides react with the amino groups on the surface of the pretreated plastic slide, while active epoxy groups on the other end of the polyfunctional epoxides react with or absorb ingredients contained in the herbs. In particular, those molecules in the ingredients of herbs that contain free hydroxyl, sulfhydryl or amino groups can form a covalent bond with the active epoxy groups on the other end of the polyfunctional epoxides, and consequently are attached onto the plastic slide. The polyfunctional epoxides preferably contain a long chemical chain of 6 to 24 carbon atoms, whereby the ingredients of herbs would not directly bind to the pretreated plastic slide. In the herbal chip of the present invention, the binding of each spot on the coated plastic slide is persistent, even after stringent stripping. In the present invention, not only macromolecules (such as proteins and DNA) but also small molecules (such as metabolites of herbs) can be immobilized in a homogeneous or heterogeneous manner on the surface of the coated plastic slide.

The preparation of the herbal chip of the present invention comprises the steps of preparing a plastic slide preferably provided with cavity chambers, pretreating plastic slide with a polyfunctional aldehyde followed by soaking in a solution of $NH_2$ group(s)-providing precursor (preferably, aqueous ammonia), coating the surface of the pretreated plastic slide with polyfunctional molecules (preferably, polyfunctional epoxides), and spotting and immobilizing on the coated plastic slide a massive amount of samples in a gridded area in microarrays with a microarrayer by applying the high-density gridding technology, wherein each of sample spots contains homogeneous or heterogeneous fractions or ingredients obtained from a herb. In the preparation of the herbal chip of the present invention, the integrating miniaturization technique can be used for increasing the density of samples gridded on the coated plastic slide.

The present invention also discloses a method of using the herbal chip for screening for active ingredients contained in herbs based on target-directed strategy, comprising the steps of loading a labeled probe(s)-containing solution onto the herbal chip (e.g. the chambers of the herbal chip) for conducting hybridization (wherein each the chambers may be covered by a glass lid for preventing the evaporation of the labeled probe(s)-containing solution), and imaging and identifying the spots that react with or bind to the labeled probe with an apparatus, e.g. a laser scanner. The label within the probes may a dye or a radioactive material.

The probes used in the present invention are homogeneous or heterogeneous, known targets based on a defined molecular mechanism, which may be, for example, small molecules, competitive ligands, or antibodies against, for example, the selected cells, receptors, enzymes, or proteins. In an embodiment of the present invention, tumor necrosis factor-alpha receptor (TNF-αR) labeled with Cy3 and strepavidin labeled with Cy5 were used as probes for conducting hybridization. Thus, for example, if a signal indicating the binding of ingredients in a spot on the herbal chip with he labeled TNF-αR is observed, there should be at least one candidates in the ingredients of the spot that exhibit a biological activity similar to anti-TNF-αR antibody. Those candidates may be useful as an antagonist for diminishing inflammatory response and then for treating autoimmune diseases, such as rheumatoid arthritis.

The herbal chip of the present invention significantly increases the throughput in the shotgun screening of biologically active ingredients contained in herbs based on the advantage that thousands of samples can be simultaneously tested. By applying the herbal chip of the present invention, any ingredient contained in herbs that exhibits a potentially pharmacological or therapeutic effect can be quickly detected, isolated and identified.

The following Example is provided to further illustrate the present invention, but the scope of the present invention should not be limited to the following Example.

EXAMPLE

Pretreatment of the Plastic Slide and Preparation of the Coated Plastic Slide

The molded plastic slide shown in FIG. 1 was made of a polymer of styrene and comprised two cavity chambers. The molded plastic slide was comparable in size with regular glass slides used in a microscope or laser scanner, wherein the depth of each of the cavity chambers is 0.05 mm.

The molded plastic slide was first immersed in 0.4% glutaldehyde solution (pH 5.0) for 4 hours at room temperature, followed by washing with water and then soaking in 3M $NH_4OH$ (pH 11.0) at 60° C. for 4 hours. The resultant plastic slide was treated with 100 mM 1,4-butanediol diglycidyl ether (pH 11.0) at 37° C. overnight. Finally, the plastic slide was washed with 0.1 M $NaHCO_3$ (pH 8.0) and then was dried.

Loading Samples onto the Coated Plastic Slide in Microarray Format

Microarrayer BioGrid (purchased from BioRobotic, Cambridge, UK) was applied to spot samples onto the above coated plastic slide. Samples were first dissolved and dispensed in 96-well microplates. A 4-pin (0.2 μm) tool was used to load samples from the 96-well microplates onto the surface of the cavity chambers of the coated plastic slide continuously, wherein the samples obtained from herbs as shown in FIG. 2A are illustrated as follows: Herb A and B were different fractions obtained from *Taraxacum mongolicum*, Herb G was a crude extract of *Taraxacum mongolicum*, Herb F was a crude extract of *Hedyotis diffuse*, Fractions 1 to 9 of Herb C were different, partially purified fractions obtained from *Hedyotis diffuse*, Herb D was a crude extract of *Lonicera japonica*, Herb E was a crude extract of *Carthamus tinctorius*, Herb J was a pure ingredient obtained from *Carthamus tinctorius*, Herb H was a crude extract of *Forsythia suspensa*, and Herb I was a crude extract of *Paeonia lactiflora*. After the spots on the surface of the cavity chambers of the Plastic slide were dried, the plastic slide was soak-treated with 1M Tris (pH 8.0) at 37° C. for 2 hours. The resultant plastic slide was then imaged by a laser scanner (Axon, USA) to make sure that all of the samples were adsorbed onto the plastic slide (see FIG. 2B).

Hybridization and Signal Detection

Tumor necrosis factor-alpha receptor (TNF-αR) labeled with Cy3 and strepavidin labeled with Cy5 were used as probes for conducting hybridization. Two glass lids were used to respectively cover the two cavity chambers of the plastic slide prior to loading 100 μl of hybridization solution (TBST buffer containing 50 mM Tris, pH 7.3, 0.15 M NaCl, and 0.02% Tween 20) containing both of the labeled probes. The plastic slide was then allowed to stand at room temperature for 4 hours, followed by washing with TBST buffer 3 times and then with water 3 times. Finally, the plastic slide was dried at 37° C. The plastic slide was imaged by the laser scanner (Axon, USA). The image result was showed in FIG. 2C.

The green fluorescent spots on the image of FIG. 2C that showed inhibition in the TNF-α/TNF-αR binding were collected. Those fractions obtained from herbs corresponding to the green fluorescent spots contained active ingredients that could bind with TNF-αR.

Biological Assay of the Samples Showing Positive Green Fluorescent Signal

Figure 3:
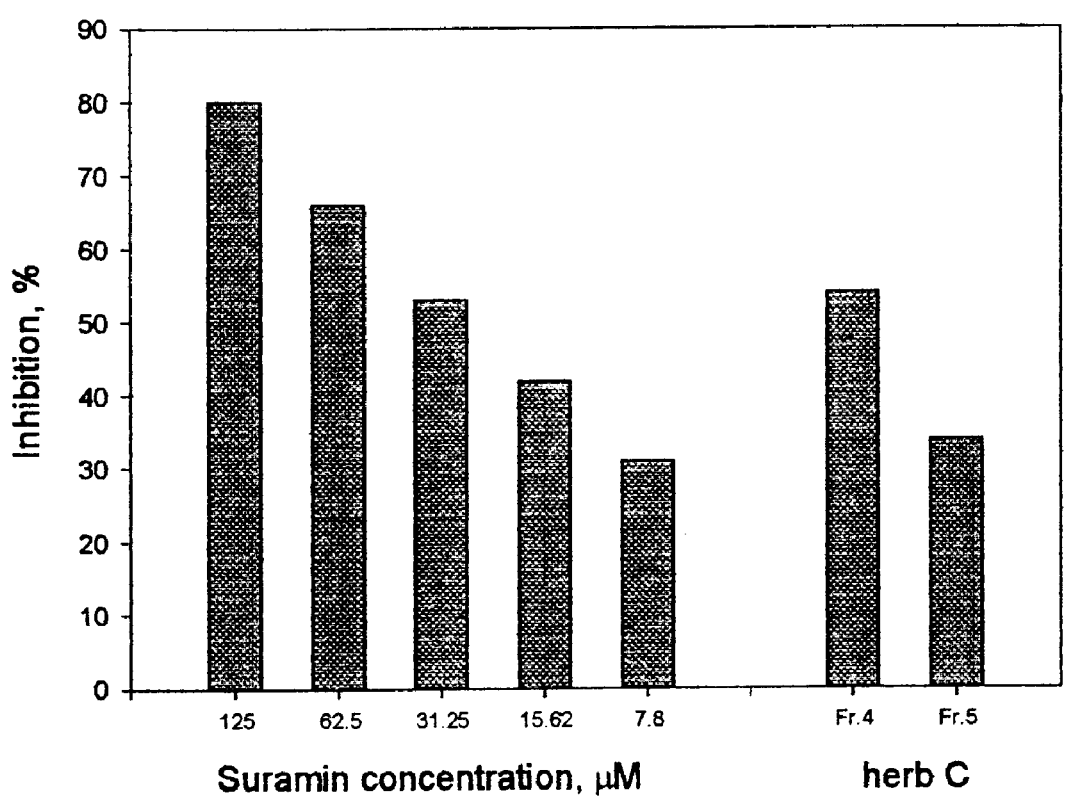
FIG. 3 shows the effect in the competitive inhibition of TNF-α/TNF-αR binding of two selected samples (fractions 4 and 5 of Herb C corresponding to the spot located at B7 and B8, and B9 and B10 of the herbal chip shown in FIG. 2A) that showed green fluorescence (Cy3) signal.

For demonstrating the biological activity of the fractions as collected above in the inhibition of TNF-α/TNF-αR binding, an assay as described in the report of Mancini et al., Biochemical Pharmacology 58: 851–859, 1999 was performed, wherein a known substance, Suramin, was used as a positive control and two samples (fractions 4 and 5 of Herb C corresponding to the spots located at B7 and B8, and B9 and B10 of the herbal chip shown in FIG. 2A) showing green fluorescence were tested. The result was shown in FIG. 3.

What is claimed is:

1. An herbal chip comprising a plastic slide, a costing on the plastic slide which binds fractions or components obtained from herbs to said slide in independently allocated microarrays on the coating, wherein said coating comprises a polyfuctional aldehyde coupled to said slide to which is coupled a compound which provides at least one $NH_2$ group, to which is bound a polyfunctional epoxide compound comprising at least one epoxide for coupling to said amino group(s) and at least one expoide which is coupled to an herbal fraction or component.

2. The herbal chip as claimed in claim 1, wherein the fractions or components obtained from herbs are homogeneous or heterogeneous.

3. The herbal chip as claimed in claim 1, wherein the fractions or components obtained from herbs are obtained by fractionating an extract of the herb by applying HPLC.

4. The herbal chip as claimed in claim 1, wherein the fractions or components obtained from herbs contain secondary metabolites of a herb.

5. The herbal chip as claimed in claim 1, wherein the material of the plastic slide is a polycarbonate, or a homopolymer or copolymer that is made of one or more monomers selected from the group consisting of ethylene, haloethylene, propylene, halopropylene, acrylate, methacrylate, butadiene, acrylonitrile, norbornene and styrene.

6. The herbal chip as claimed in claim 5, wherein the plastic slide is made of a polymer of styrene.

7. The herbal chip as claimed in claim 1, wherein the plastic slide has two cavity chambers.

8. The herbal chip as claimed in claim 1, wherein the polyfunctional aldehyde is glutaldehyde.

9. The herbal chip as claimed in claim 1, wherein the $NH_2$ group(s)-providing compound is $NH_4OH$.

10. The herbal chip as claimed in claim 1, wherein the epoxy group(s) which couple to the herb components or fractions react with the free hydroxyl, sulfhydryl or amino groups.

11. The herbal chip as claimed in claim 1, wherein the epoxide compound contains a long chemical chain of 6 to 24 carbon atoms.

12. A method of producing the herbal chip as claimed in claim 1, comprising the step of coupling the herbal fractions or components to said epoxide contained in said coating for coupling to an herbal fraction or component.

13. The method as claimed in claim 12, wherein the plastic slid has two cavity chambers and the samples are spotted or immobilized on the surface of the cavity chamber.

14. The method as claimed in claim 12, wherein said coupling is preceded by the steps of treating the slide with said polyfunctional aldehyde followed by soaking in a solution of said $NH_2$-providing compound, and treating with said polyfunctional epoxide compound.

15. The method as claimed in claim 14, wherein the polyfunctional aldehyde is glutaldehyde.

16. The method as claimed in claim 14, wherein the $NH_2$-providing precursor is $NH_4OH$.

17. The method at claimed in claim 12, wherein the polyfunctional epoxide compound contains at least on epoxy group at each of its ends.

18. A method of using the herbal chips as claimed in claim 1 for screening for active ingredients contained in herbs, comprising the steps of loading a labeled probe(s)-containing solution onto the herbal chip for conducting hybridization, and imaging and identifying the gridded samples that react with or bind to the probe.

19. The method as claimed in claim 18, wherein the labeled probe(s)-containing solution is homogeneous or heterogeneous.

20. The method as claimed in claim 18, wherein the label is a dye or a radioactive material.

* * * * *